(12) United States Patent
Lee et al.

(10) Patent No.: US 10,041,867 B2
(45) Date of Patent: Aug. 7, 2018

(54) FLEXIBLE DEVICE, AND APPARATUS, METHOD AND COMPUTER-READABLE RECORDING MEDIUM FOR DETECTING SHAPE OF FLEXIBLE DEVICE

(71) Applicant: Samsung Electronics Co., Ltd., Suwon-si, Gyeonggi-do (KR)

(72) Inventors: Hyung Sun Lee, Yongin-si (KR); Youn-Ho Choi, Seoul (KR); Seok-Myong Kang, Hwaseong-si (KR); Shi-Yun Cho, Anyang-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 872 days.

(21) Appl. No.: 14/273,027

(22) Filed: May 8, 2014

(65) Prior Publication Data

US 2014/0331781 A1 Nov. 13, 2014

(30) Foreign Application Priority Data

May 8, 2013 (KR) ........................ 10-2013-0051925

(51) Int. Cl.
*G01N 3/20* (2006.01)
*G01B 5/20* (2006.01)
*G01B 5/30* (2006.01)
*G06F 1/16* (2006.01)
(Continued)

(52) U.S. Cl.
CPC ................ *G01N 3/20* (2013.01); *G01B 5/20* (2013.01); *G01B 5/30* (2013.01); *G06F 1/1626* (2013.01); *G06F 1/1652* (2013.01); *G06F 3/0487* (2013.01); *H04M 1/0268* (2013.01); *H04M 2250/12* (2013.01)

(58) Field of Classification Search
CPC ....................................................... G01N 3/20
USPC ........................................................... 73/849
See application file for complete search history.

(56) References Cited

U.S. PATENT DOCUMENTS 7,298,236 B2 11/2007 Chen
9,256,298 B2 * 2/2016 Zhou .................... G09G 3/20
9,459,736 B2 * 10/2016 Badaye ................ G06F 3/0416
(Continued)

FOREIGN PATENT DOCUMENTS

CN 102 629 446 A 8/2012
EP 2508960 A2 10/2012
WO WO 2012135935 A2 * 10/2012 ........... G06F 1/1626

OTHER PUBLICATIONS

Measurements Group, Inc., "Errors Due to Transverse Sensitivity in Strain Gages", Experimental Techniques, Jan. 30, 1983, pp. 30-35, vol. 7, No. 1.

*Primary Examiner* — Lisa Caputo
*Assistant Examiner* — Jamel Williams
(74) *Attorney, Agent, or Firm* — Jefferson IP Law, LLP (57) ABSTRACT

A flexible device including sensors for shape detection is provided. The flexible device includes a measurement unit including a plurality of bending sensors disposed along at least one edge of the flexible device, and configured to output measurement values sensed by the plurality of bending sensors, and a controller configured to detect a position of at least one curve point on the flexible device by receiving the sensed measurements values from the measurement unit, and to detect at least one bending line of the flexing device according to information about positions of curve points, which are detected on at least two different sides of the flexible device.

11 Claims, 7 Drawing Sheets

(51) Int. Cl.
 *G06F 3/0487* (2013.01)
 *H04M 1/02* (2006.01)

(56) References Cited

U.S. PATENT DOCUMENTS

| | | | |
|---|---|---|---|
| 2005/0006010 A1 | 1/2005 | Benedictus et al. | |
| 2006/0238494 A1* | 10/2006 | Narayanaswami | G06F 3/002 345/156 |
| 2007/0085845 A1 | 4/2007 | Kikuchi et al. | |
| 2007/0132726 A1 | 6/2007 | Moriyama | |
| 2009/0256817 A1* | 10/2009 | Perlin | G06F 3/0233 345/174 |
| 2010/0011291 A1* | 1/2010 | Nurmi | G06F 3/0414 715/702 |
| 2012/0038613 A1* | 2/2012 | Choi | G06F 1/1652 345/211 |
| 2012/0139834 A1* | 6/2012 | Han | G06F 3/03 345/157 |
| 2013/0044052 A1* | 2/2013 | Hong | G06F 3/0414 345/156 |
| 2014/0125578 A1* | 5/2014 | Zhou | G09G 3/20 345/156 |
| 2014/0179380 A1* | 6/2014 | Roh | H04M 1/6033 455/569.1 |

* cited by examiner

FLEXIBLE DEVICE, AND APPARATUS, METHOD AND COMPUTER-READABLE RECORDING MEDIUM FOR DETECTING SHAPE OF FLEXIBLE DEVICE

CROSS-REFERENCE TO RELATED APPLICATION(S)

This application claims the benefit under 35 U.S.C. § 119(a) of a Korean patent application filed on May 8, 2013 in the Korean Intellectual Property Office and assigned Serial number 10-2013-0051925, the entire disclosure of which is hereby incorporated by reference.

TECHNICAL FIELD

The present disclosure relates to a flexible device. More particularly, the present disclosure relates to a flexible device equipped with sensors for shape detection, and an apparatus, a method and a computer-readable recording medium for detecting a shape of the flexible device depending on strain corresponding to the flexible device.

BACKGROUND

Due to the rapid development of display technology for processing and displaying large amounts of information, a wide variety of display devices have been introduced.

Liquid Crystal Display (LCD) devices, Plasma Display Panel (PDP) devices, Field Emission Display (FED) devices, Electro Luminescence Display (ELD) devices and the like have been developed as examples of the display devices. These display devices have evolved, seeking thinness, a light weight and low-power consumption. However, the above-mentioned display devices may have limitations in implementing the thinness, the light weight and flexibility, since the display devices use a glass substrate to withstand the high heat generated during the manufacturing process.

In recent years, therefore, as next-generation flat display devices, flexible display devices have emerged and are manufactured to maintain display performance even though the display devices are bent, like paper may be bent, as the display devices use a bendable flexible material like plastic film, instead of inflexible glass substrate. As for these flexible display devices, users may bend or roll the display devices, while carrying the devices with and/or upon themselves, since the flexible display devices are not only thinner and lighter, but also impact-resistant and bendable. In addition, since the flexible display devices may be manufactured in a variety of shapes or forms, their utilization may be expanded in the future.

Mass production of the flexible display devices may occur as the flexible display technology has undergone field tests. Flexible devices based on the flexible display are expected to provide a new type of input/output interface different from that of related art electronic devices having a rigid display, making it possible to provide new user experiences.

Many related art flexible display-related technologies have proposed methods of detecting a change in a shape of devices to change contents displayed on a display or to change tactile, haptic, and acoustic feedbacks.

For example, the proposed methods may include a method of detecting bending of a flexible display to execute a function linked to a graphic object existing in a position where a bending line is formed, and a method of linking strain of a flexible display to a computer's control command to control a speed of flipping pages displayed on the screen depending on a degree of bending.

In addition to these technologies, many studies have been conducted on various application technologies for detecting bending of flexible devices, to switch an execution mode, change a User Interface (UI) structure, adjust a scrolling speed, and/or execute an associated menu depending on the change in shape of the flexible devices.

However, these related-art technologies present no specific methods capable of effectively detecting a change in shape by actually using various sensors, although the related-art technologies have proposed ways to detect a change in shape using sensors mounted on a flexible device, e.g., a flexible display.

In addition, in order to detect bending of a flexible device and to apply detection information in a variety of ways, there is a need to detect bending of the flexible device and also to detect a more accurate and precise position and degree of the bending. However, there is a limit to accurately and precisely detecting the bending, because various components are mounted in a flexible device, the flexible device needs to provide functions of a display by itself, and each flexible device is different in terms of the device thickness and the bending strength.

Therefore, there is a need for a method capable of more accurately and precisely detecting a change in a shape of a flexible device depending on strain corresponding to the flexible device if the flexible device undergoes strain.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a flexible device that includes a plurality of bending sensors disposed on edges of the flexible device and that is configured to detect a shape of the flexible device from the plurality of disposed sensors, and an apparatus, a method and a computer-readable recording medium for detecting a shape of the flexible device.

Another aspect of the present disclosure is to provide a flexible device that includes a plurality of bending sensors disposed on edges of the flexible device and that are configured to detect a strained shape of the flexible device by detecting curve points of the flexible device from the plurality of disposed sensors to detect a bending line, and an apparatus, a method and a computer-readable recording medium for detecting a shape of the flexible device.

Another aspect of the present disclosure is to provide a flexible device that includes a plurality of bending sensors disposed on edges of the flexible device and that are configured to detect a strained shape of the flexible device by detecting curve points of the flexible device from the plurality of disposed sensors in order to detect a bending line and to provide information, such as a position, a slope, a thickness, and a direction of the detected bending line, and an apparatus, a method and a computer-readable recording medium for detecting a shape of the flexible device.

In accordance with an aspect of the present disclosure, a flexible device is provided. The device includes a measurement unit including a plurality of bending sensors disposed along at least one edge of the flexible device, and configured to output measurement values sensed by the plurality of bending sensors, and a controller configured to detect a position of at least one curve point on the flexible device by receiving the sensed measurements values from the measurement unit, and to detect at least one bending line of the flexing device according to information about positions of curve points, which are detected on at least two different sides of the flexible device.

In accordance with another aspect of the present disclosure, an apparatus for detecting a shape of a flexible device is provided. The apparatus includes a curve point detector configured to detect a position of at least one curve point on the flexible device by receiving sensed measurement values from at least one of a plurality of bending sensors disposed along edges of the flexible device, and a bending line detector configured to detect at least one bending line of the flexible device according to information about positions of curve points which are detected on at least two different sides of the flexible device by the curve point detector.\

In accordance with further another aspect of the present disclosure, a method for detecting a shape of a flexible device is provided. The method includes receiving sensed measurement values from a plurality of bending sensors disposed along edges of the flexible device, detecting a position of at least one curve point on the flexible device based on the received measurement values, and detecting at least one bending line of the flexible device based on information about the detected position of the at least one curve point detected on at least two different sides of the flexible device.

In accordance with yet another aspect of the present disclosure, a computer-readable recording medium storing information for causing a computer to perform a method of detecting a shape of a flexible device is provided.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, like reference numerals will be understood to refer to like parts, components, and structures.

DETAILED DESCRIPTION

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

An aspect of the present disclosure provides an apparatus and method capable of more accurately and efficiently detecting a strained shape of a flexible device, e.g., a flexible display, such as a shape in which the flexible device is bent, twisted, stretched, or a modified in any similar and/or suitable manner. In accordance with an embodiment of the present disclosure, the apparatus and method may detect a bending line of a flexible device according to measurement values sensed by a plurality of sensors disposed on the flexible device, and may extract and provide feature information of the bending line, such as a position, a slope, an angle, a thickness and a direction of the detected bending line.

To this end, the apparatus and method may include a plurality of bending sensors disposed on edges of the flexible device, and may detect a bending line by detecting curve points of the flexible device from the plurality of disposed sensors. The apparatus and method may provide the flexible device's components with feature information such as a position, a slope, an angle, a thickness and a direction of the detected bending line, thereby providing a variety of services which are based on strain information of the flexible device.

A flexible device in the present disclosure may be any device equipped with a flexible display, and may be referred to as a portable terminal, a mobile terminal, a communication terminal, a portable communication terminal, a portable mobile terminal and the like. For example, the flexible device may be a smart phone, a cellular phone, a game console, a Television (TV), a display device, a car head unit, a notebook computer, a laptop computer, a tablet computer, a Personal Multimedia Player (PMP), a Personal Digital Assistants (PDA), a navigation device, an Automatic Teller Machine (ATM) for banks, a Point of Sale (POS) for shops, and the like. As for the flexible device in the present disclosure, any bendable device including, for example, a flexible display, may correspond to a flexible device according to an embodiment of the present disclosure, and the flexible device is not necessarily limited to the flexible display device.

For a better understanding of the present disclosure, various embodiments of the present disclosure will be described in detail below with reference to the accompanying drawings.

Figure 1:
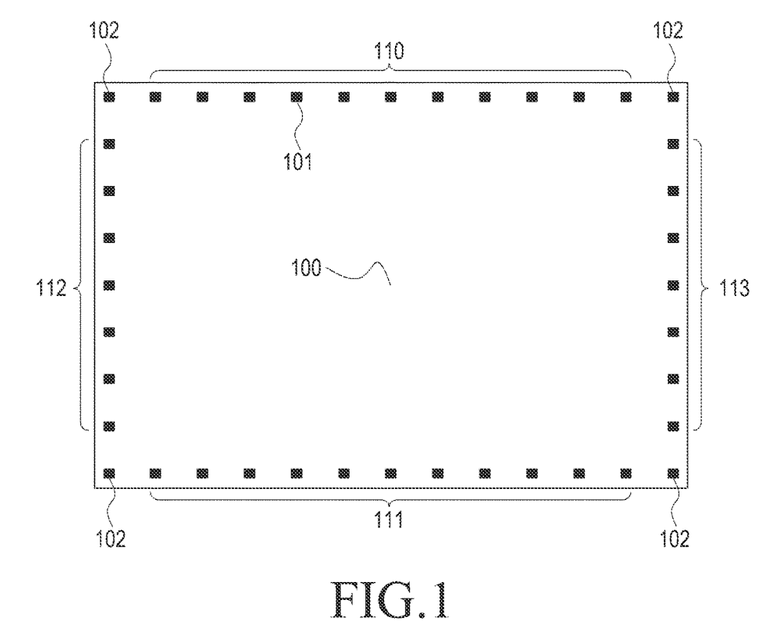
FIG. 1 illustrates a flexible device on which a plurality of bending sensors is disposed according to an embodiment of the present disclosure.

FIG. 1 illustrates a flexible device on which a plurality of bending sensors is disposed according to an embodiment of the present disclosure.

Referring to FIG. 1, bending sensors 101 and 102 detect and/or sense bending of a flexible device 100 and may be disposed along edges of the flexible device 100 at regular intervals. The plane of the flexible device 100 may have a variety of shapes, such as a circle, an oval, a rhombus, a trapezoid, a rectangle and a square, and in FIG. 1, the plane of the flexible device 100 is assumed to be rectangular in a shape according to an embodiment of the present disclosure.

Various types of the bending sensors 101 and 102 may be applied. For example, strain gauges may be applied according to an embodiment of the present disclosure.

If the plane of the flexible device 100 is rectangular in shape, as illustrated in FIG. 1, edges of the flexible device 100 may be divided into a first outer region 110, a second outer region 111, a third outer region 112, and a fourth outer region 113.

Each of the bending sensors 101 and 102 may be disposed on each side and/or edge of the flexible device 100 to detect a direction, such as a perpendicular direction, in which the flexible device 100 is bent. Accordingly, the bending sensors 101 disposed in the first and second outer regions 110 and 111 may determine and/or detect a bending line formed when the flexible device 100 is bent along a vertical line, and the bending sensors 101 disposed in the third and fourth outer regions 112 and 113 may determine a bending line formed when the flexible device 100 is bent along a horizontal line.

The bending sensor 101, which may be a strain gauge 101, may have a directionality, and thus may recognize bending in one direction. If a pair of sensors is disposed in each disposition position perpendicular to a sensing direction of a respective sensor, the bending may be detected more accurately. Alternatively, one sensor may be disposed in each disposition position to detect a direction perpendicular to each of the outer regions 110, 111, 112 and 113.

In accordance with an embodiment of the present disclosure, if the plane of the flexible device 100 is polygonal, e.g., rectangular, in shape, the sensors 102 may be added or disposed even at the corners rather than on each side and/or edge. The corner sensors 102 may be disposed by variously setting sensing directions thereof. For example, the corner sensors 102 may be disposed to match the direction of the sensors disposed in the first outer region 110 and/or the second outer region 111, or the corner sensors 102 may be disposed to match the direction of the sensors disposed in the third outer region 112 and/or the fourth outer region 113. As another example, the corner sensors 102 may be disposed by tilting the sensing direction thereof at an angle of 45°, to determine whether each corner is bent.

In other words, the corner sensors 102 may be used to distinguish special cases where the bending of the flexible device 100 may be not detected by the sensors 101 disposed on each of the sides. For example, in a case where there are no corner sensors 102, the same sensor values may be output even for different types of bending. The types of bending may be distinguished according to the corner sensors 102. For example, in a case where strain gauges are used as examples of the sensors 101 and 102, the strain gauges may determine bending in one direction as the strain gauges have directionality corresponding to the one direction.

In a case where sensors cannot be directly mounted on the flexible device 100, or where a detectable amount of strain is not applied to the strain gauges due to the structural factors of a display module, sensors may be mounted on a flexible substrate that is disposed to be parallel to a display plane. Alternatively, strain gauges may be implemented on the same substrate as that of the flexible display.

In a case where the flexible device 100 is a flexible display device, the flexible device 100 may include a flexible display, a flexible printed circuit board, and a strain gauge array. Components of the flexible display device may be implemented such that two or more components may be combined into a single component, or one component may be subdivided into two or more components, if necessary.

The flexible device 100, as described above, may be applied to cellular phones, smart phones, portable Personal Computers (PCs), e.g., netbook PCs, smart-book PCs, laptop computers, notebook computers, and the like, e-Books, TVs, digital broadcasting terminals, Personal Digital Assistants (PDAs), Portable Multimedia Players (PMPs), Motion Picture Expert Group (MPEG) Audio Layer 3 (MP3) players, navigation devices, and the like.

If the flexible device 100 is a flexible display device, the flexible device 100 may include a flexible display and/or electronic paper (e-paper) as a display that may be bent, folded and/or rolled using a flexible material like plastic. The flexible display in the present disclosure may include a rugged display that is lightweight and unbreakable as it is manufactured on a thin flexible substrate, which can be bent, folded and/or rolled, like paper, while maintaining the intact display characteristics of the existing flat display. The flexible display may include a substrate, e.g., flexible plastic, metallic thin film, thin glass and the like, a driving unit, e.g., a-si, a Thin Film Transistor (TFT), Low Temperature Poly Silicon (LTPS) TFT, an Organic TFT (OTFT), an oxide TFT, a nano TFT, and the like, for driving a flexible display unit, so as to provide Electro-Luminescence (EL), and the like, and a display, and a protective film for protecting the display unit.

The flexible display may display status information and/or an indicator generated during an operation of the flexible display device, limited numbers and characters, moving pictures, still pictures, and the like.

The flexible printed circuit board may be firmly attached onto edges of the front and/or rear of the flexible display unit in a form of a strip, and the flexible printed circuit board may be attached as a polyimide substrate by double-sided tape, bonding and the like.

The strain gauge array may be bending sensors for detecting bending of a flexible display according to an embodiment of the present disclosure. The strain gauge array may be disposed on the flexible printed circuit board, for each channel, and may include a plurality of strain gauges disposed to be spaced apart at regular intervals or disposed in any suitable and/or similar manner.

The strain gauge is a sensor that may be bent as described above, and since the strain gauge detects a resistance that varies in proportion to a degree of bending, the strain gauge may detect bending of the flexible display, which corresponds to a position where the strain gauge is disposed, and to calculate a degree of the bending in an embodiment of the present disclosure.

In an embodiment of the present disclosure, the term 'bending' may refer to flexing, folding, curling, rolling, and the like.

Specifically, if the flexible device 100, e.g., the flexible display is bent, the strain gauges may also be bent along the flexible device 100, because the strain gauges are mounted on the flexible printed circuit board that is attached onto edges of the flexible device 100. As the strain gauges are bent, their cross-sectional area may decrease due to an increase in length of resistance wires mounted therein, so electrical resistances may increase. By measuring the increasing resistances, the strain gauges may detect and measure bending of the flexible display. The strain gauges may measure a resistance of each sensor upon occurrence of bending, because multiple strain gauges are disposed on edges of the flexible device 100.

In a case where not all the components included in the flexible device 100 may have a flexibility because the flexible display device used as an example of the flexible device 100 may have components responsible for various functions, such as an operator, a battery and a communication module, in addition to the display, solid components may need to be disposed in regions, e.g., outer regions 110, 111, 112 and 113, to which one or more edges belong. In this case, in an embodiment of the present disclosure, bending lines crossing the flexible edges may be detected.

More specifically, a strain gauge may correspond to a resistor having two terminals. Therefore, the strain gauge may have a characteristic such that a resistance between terminals varies according to a physical elongation and contraction. In order to detect a shape of the flexible device 100 using these sensors, a measurement unit corresponding to signal processing is needed, and may be implemented as illustrated in FIG. 2.

Figure 2:
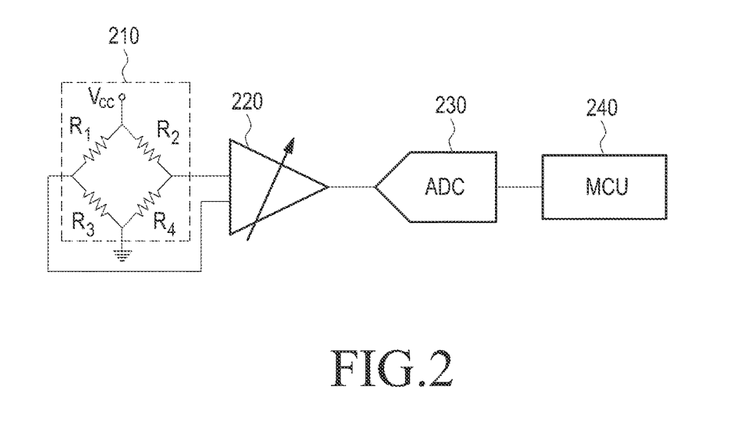
FIG. 2 illustrates a structure of a measurement unit according to an embodiment of the present disclosure.
Figure 3A:
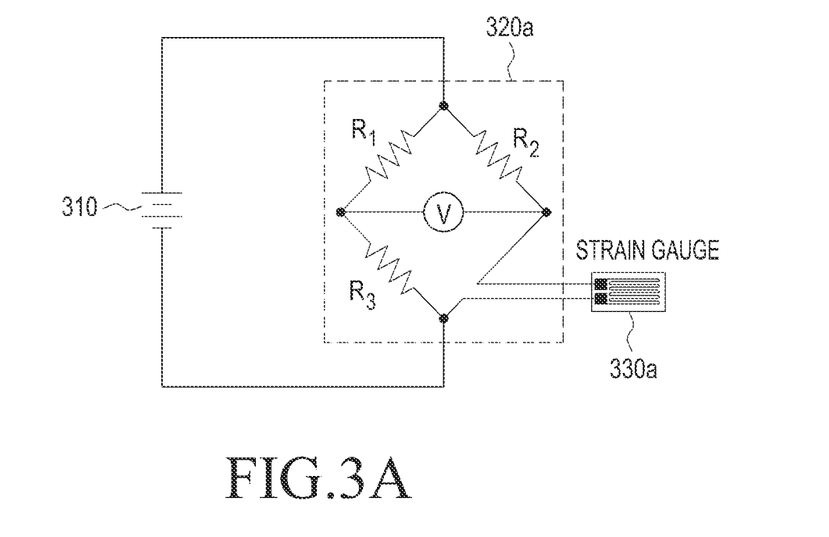
FIGS. 3A and 3B illustrate different examples of a strain gauge circuit according to an embodiment of the present disclosure.
Figure 3B:
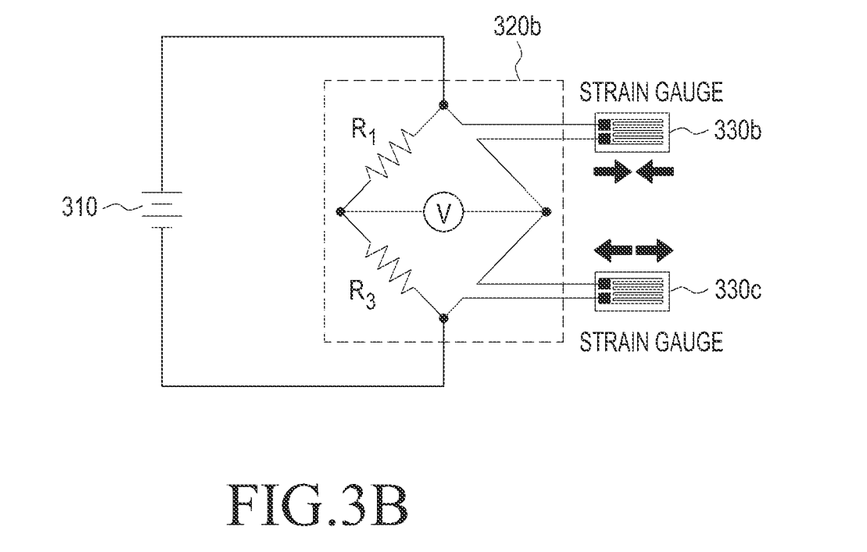

FIG. 2 illustrates a structure of a measurement unit according to an embodiment of the present disclosure; and FIGS. 3A and 3B illustrate different examples of a strain gauge circuit according to an embodiment of the present disclosure.

Referring to FIGS. 2, 3A, and 3B, the measurement unit may include a bridge circuit 210, an amplifier 220, an Analog-to-Digital Converter (ADC) 230, and a Micro Controller Unit (MCU) 240.

The bridge circuit 210 may be implemented as a Wheatstone bridge including one or more strain gauges. Because variation in resistance of the strain gauges is very small in most cases, a change in resistance may be converted into a change in voltage by the Wheatstone bridge and the change in voltage may be amplified by the amplifier 220, as illustrated in FIG. 2.

In accordance with an embodiment of the present disclosure, the Wheatstone bridge may use a quarter-bridge circuit for detecting a change in resistance of one strain gauge, as illustrated in FIG. 3A, or may use a half-bridge circuit for detecting a change in resistance of a pair of strain gauges, which may undergo elongation and contraction conversely, as illustrated in FIG. 3B. Specifically, in a case where one strain gauge is mounted on each of both sides in each disposition position where the sensors 101 and 102 are disposed on the flexible device 100 in FIG. 1, two strain gauges may conversely detect a change in elongation or contraction, thereby contributing to improvement of the sensitivity of the sensors.

In a case where the bridge circuit 210 in FIG. 2 is constructed with a quarter-bridge circuit 320a, as illustrated in FIG. 3A, resistors R1, R2 and R3, and a strain gauge 330a may constitute the quarter-bridge circuit 320a, and if power is distributed to each of the resistors R1, R2, and R3, as power of a power supply 310 is supplied, a value of the voltage output from the bridge circuit may significantly vary according to the change in resistance of the strain gauge 330a.

In a case where the bridge circuit 210 in FIG. 2 is constructed with a half-bridge circuit 320b, as illustrated in FIG. 3B, resistors R1 and R3 and strain gauges 330b and 330c may constitute the half-bridge circuit 320b, and if power is distributed to each the resistors R1 and R3 as power of the power supply 310 is supplied, a value of the voltage output from the bridge circuit 210 may significantly vary depending on the change in resistance of each of the strain gauges 330b and 330c. Based on the voltage value output from the bridge circuit, a shape of the flexible device may be detected according to a method described below.

Referring back to FIG. 2, the output voltage of the bridge circuit 210 is input to the amplifier 220, in which a small voltage value may be amplified into a large voltage value. A Variable Gain Amplifier (VGA), or any other similar and/or suitable amplifier, may be used as the amplifier 220. The variable gain amplifier may match a range of the output voltage with an input voltage of the analog-to-digital converter 230 or a next block.

In accordance with an embodiment of the present disclosure, a wide voltage measurement range and its fine resolution may be obtained by controlling a gain of the amplifier 220 according to the output voltage of at least one of the strain gauges.

In a case where a plurality of bending sensors 101 and 102 are disposed according to an embodiment of the present disclosure, as illustrated in FIGS. 3A and 3B, a multiplexer (not shown), e.g., an analog multiplexer, may be interposed between a plurality of bridge circuits 210 and the amplifier 220 to amplify and convert the output of each of the sensors 101 and 102. By doing so, a burden of a cost for the amplifier 220 may be reduced due to an increase in the number of sensors.

In the measurement unit, the ADC 230 may convert an analog input signal into a digital value, and may provide the digital value the MCU 240, wherein the MCU 240 may be a microprocessor, a microcontroller, an Integrated Circuit (IC), and/or any other similar and/or suitable hardware element.

The MCU 240 constituting the measurement unit may detect a shape of the flexible device 100 according to the measurement values sensed by the sensors according to an embodiment of the present disclosure. Therefore, the whole or at least a part of the apparatus for detecting a shape of a flexible device according to an embodiment of the present disclosure may correspond to the whole or at least a part of the MCU 240. Each of the function blocks constituting the MCU 240 may be implemented in one or more controller ICs, or may be implemented in various ways, for example, by a software block which is executed in an independent hardware arithmetic circuit or a microcontroller.

Figure 4:
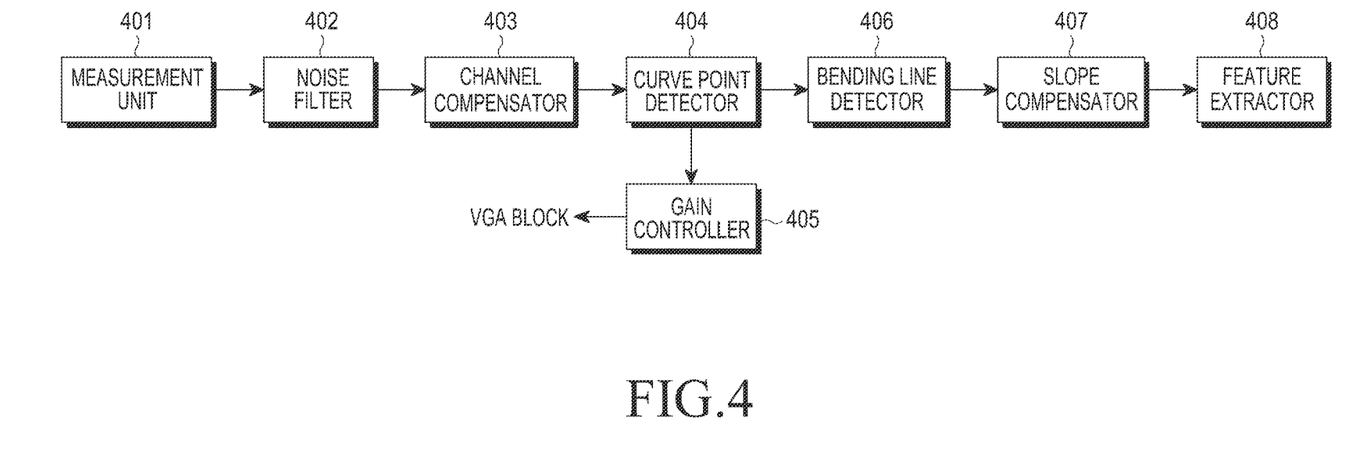
FIG. 4 is a block diagram illustrating a detailed structure of an apparatus for detecting a shape of a flexible device according to an embodiment of the present disclosure.
Figure 5:
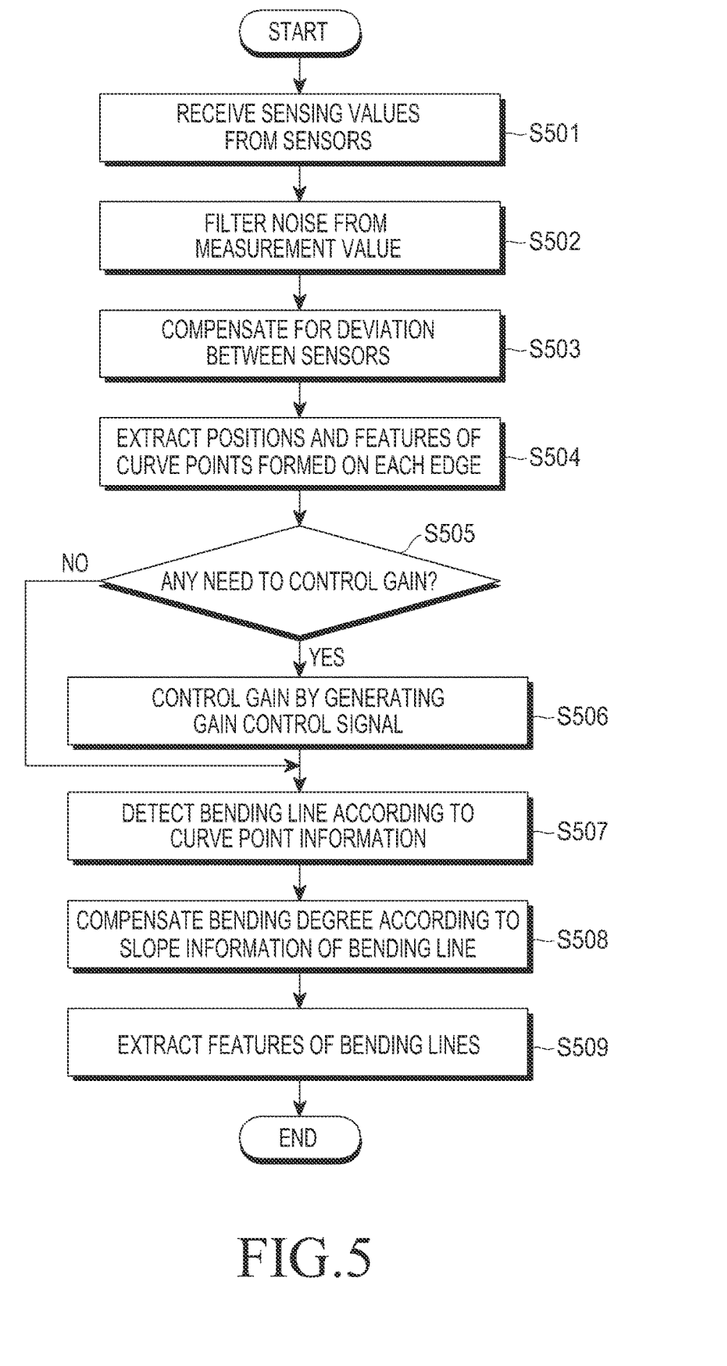
FIG. 5 is a flowchart illustrating a procedure for detecting a shape of a flexible device according to an embodiment of the present disclosure.

Reference will now be made to FIGS. 4 and 5 to describe in detail the apparatus and method according to various embodiments of the present disclosure.

FIG. 4 is a block diagram illustrating a detailed structure of an apparatus for detecting a shape of a flexible device according to an embodiment of the present disclosure.

Referring to FIG. 4, the apparatus may include a measurement unit 401, a noise filter 402, a channel compensator 403, a curve point detector 404, a gain controller 405, e.g., a VGA gain controller, a bending line detector 406, a slope compensator 407, and a feature extractor 408. The apparatus according to an embodiment of the present disclosure may be implemented by selectively adding or removing at least one of the above function blocks.

The noise filter 402 may filter out, from a signal, a change in sensor value that due to a cause other than a user's bending action, in the flexible device 100.

The channel compensator 403 may compensate for a deviation between sensors disposed on the flexible device 100, and may also compensate for a deviation between different sensors, for each of flexible devices 100. To this end, the channel compensator 403 may compensate each sensor value by taking advantage of the compensation values which were measured in advance by calibration.

The curve point detector 404 may analyze measurement values, e.g., voltage values, sensed by the sensors 101 and 102 disposed on each side and/or edge in a row, to extract positions and features of curve points formed on each edge, e.g., each outer region.

The gain controller 405 may generate a proper gain control signal and provide it to the amplifier 220, if there is a need to control a gain of the amplifier 220, e.g., if it is determined, based on the output value of the curve point detector 404, that an output of each of the sensors 101 and 102 is less than a predetermined threshold, or is out of an input range of the ADC 230.

The curve point information detected from each of the outer regions 110, 111, 112 and 113, by the curve point detector 404, may be input to the bending line detector 406, and used to detect a shape of the flexible device 100.

As illustrated in FIG. 1, the sensor arrangement structure, according to an embodiment of the present disclosure, may not uniformly acquire two-dimensional bending information over entire surface of the flexible device 100. In some cases, two or more different shapes may cause the same sensor output. Therefore, the bending line detector 406 may output the shape detection results which are most pertinent to each situation, taking into account exceptional cases according to an embodiment of the present disclosure.

The slope compensator 407 may compensate bending information of a bending line according to the slope information of the bending line. Since the sensor arrangement structure, according to an embodiment of the present disclosure, is configured to detect bending in a direction perpendicular to each side and/or edge corresponding to each of the outer regions 110, 111, 112 and 113 in the position of each of the sensors 101, as illustrated in FIG. 1, a value of the output may be affected according to an angle formed between the bending line and each side and/or edge of the flexible device 100 even though the shape of the flexible device 100 is strained with the same radius of curvature. For example, the largest value may be output when the bending line is perpendicular to each side, and the output value is getting smaller as the bending line is inclined away from the perpendicular direction. Therefore, the slope compensator 407 may compensate bending information of the bending line according to the slope information of the bending line.

The feature extractor 408 may extract features of the detected bending lines and deliver the extracted features to an upper layer, e.g., an application. A set of several features capable of uniquely expressing the bending lines may be used as extractable features of the bending lines. For example, a set of a position, a slope, an angle, a thickness, a direction and the like of each bending line may be used as extractable features of the bending lines.

For example, a position of one of the bending lines that corresponds to the strain of a shape of the flexible device may be expressed with the coordinates of the center of mass for a line connecting a start point and an end point of the flexible device, and in this case, a slope may be expressed with an angle that is formed between a vertical line and the bending line when the flexible device is situated in a specific reference direction. An angle of the bending line may be an angle at which a first tangent plane, which is on a line where strain of the bending line starts, crosses a second tangent plane, which is on a line where strain of the bending line ends. Since two lines having the same slope and the same angle in the same position may be strained over regions of different sizes, the sizes of these regions may be expressed according to a thickness of bending line. An angle of the bending line represents a difference that the strain of the device appears convex or concave on the basis of the direction in which the user takes a look at the device.

The components of the apparatus are separately shown in the drawing to indicate that the components may be separated in terms of the functions and logics, and it doesn't mean that the components should be physically separate components or should be implemented with separate codes.

The term 'function', as used herein, may refer to a functional and/or structural combination of hardware for implementing technical operations of the disclosure and software for driving the hardware. For example, each function may be a logical unit of a predetermined code and hardware resources for implementing the predetermined code, and it will be apparent to those of ordinary skill in the art that the function does not necessarily mean a physically connected code, or one type of hardware.

FIG. 5 is a flowchart illustrating a procedure for detecting a shape of a flexible device according to an embodiment of the present disclosure.

Referring to FIG. 5, an apparatus according to an embodiment of the present disclosure may receive measurement values sensed by a plurality of sensors disposed on edges of the flexible device in operation S501. The measurement values may be the values, e.g., 14-bit digital values associated with a graph shown in FIG. 7, which are obtained by amplifying an output voltage of the bridge circuit and converting the amplified voltage into a digital signal as described above. Thereafter, the apparatus may filter a noise signal from the measurement values in operation S502, and the apparatus may compensate for a deviation between the sensors in operation S503.

The apparatus may extract positions and features of curve points formed on each edge in operation S504. The apparatus determines, based on the output values of the curve point detector 404, whether there is a need to control a gain of the amplifier 220 provided in the measurement unit in operation S505. If in operation S505, the apparatus determines that gain of the amplifier 220 is to be controlled, then the apparatus may control gain by generating a gain control signal and may provide it to the amplifier 220 in operation S506.

The apparatus may detect at least one bending line according to the curve point information in operation S507. The apparatus may optionally compensate a bending degree of bending according to the slope information of the bending line in operation S508. The apparatus may extract at least one feature, e.g., a position, a slope, an angle, a thickness, a direction and the like of a bending line, of each of the detected bending lines in operation S509.

The method of detecting a shape of a flexible device, according to an embodiment of the present disclosure, may be implemented in a form of computer instructions that may be executed by a variety of computer devices, elements, and/or units, and may be written in a computer-readable medium. The computer-readable medium may include program instructions, data files and data structures individually or in combination. The program instructions written in the computer-readable medium may be program instructions which are specially designed and constructed for the present disclosure, or may be available program instructions known to those skilled in the art of computer software. Examples of the computer-readable recording medium may include magnetic media, e.g., a hard disk, a floppy disk, and a magnetic tape, optical media, e.g., a Compact Disk-Read Only Memory (CD-ROM), and a Digital Versatile Disk (DVD), magneto-optical media, e.g., a floptical disk, and hardware devices, e.g., a Read Only Memory (ROM), a Random Access Memory (RAM), and a flash memory, which are specially configured to store and execute program instructions. Examples of the program instructions may include not only the machine code created by compiler, but also the high-level language code that can be executed by a computer using an interpreter and the like. The hardware device may be configured to operate as one or more software modules to perform an operation of the present disclosure, and vice versa.

Reference will now be made to FIGS. 7 to 11 to describe in more detail examples of various embodiments of the present disclosure, implemented in a flexible device, and examples of an operation thereof.

Figure 6:
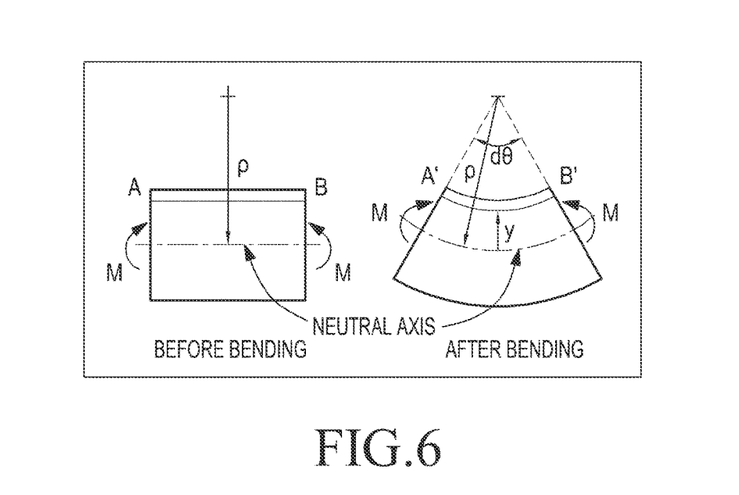
FIG. 6 illustrates a change in strain due to bending of a flexible device according to an embodiment of the present disclosure.

If a user bends, in a specific direction, a flexible device, e.g., a mobile device and/or a flexible display, in which a plurality of sensors are disposed on edges, according to an embodiment of the present disclosure, as illustrated in FIGS. 3A and 3B, sensors affected by the bending, from among the plurality of sensors disposed on one or both sides of the flexible device, e.g., a substrate in the device, may undergo strain as illustrated in FIG. 6.

FIG. 6 illustrates a change in strain due to bending of a flexible device according to an embodiment of the present disclosure.

Referring to FIG. 6, if an axis, whose length is not changed despite the bending of the flexible device, is referred to as a neutral axis, a distance between the neutral axis and a position of the sensor is defined as y, a length of the sensor is given as a line AB, and a radius with which the substrate is bent is defined by ρ, then strain ε may be expressed as Equation (1) below.

$$\varepsilon = \frac{A'B' - AB}{AB} = \frac{(\rho - y)\theta - \rho\theta}{\rho\theta} = -\frac{y}{\rho} \qquad \text{Equation (1)}$$

A strain gauge, which may be used as a bending sensor, may be a sensor that determines and/or detects a linear change in resistance according to the change in strain. Therefore, a ratio K of a change in resistance to strain is called a gauge factor, and each material used may have a different value of K. This may be represented by Equation (2) below.

$$\frac{\Delta R}{R} = K\varepsilon = -K\frac{y}{\rho} \qquad \text{Equation (2)}$$

As for sensors, such as the sensors illustrated in FIG. 1, their resistance may vary according to the bent shape of the flexible device. Therefore, a voltage output being proportional to a degree of bending may be obtained by configuring a Wheatstone bridge circuit, as illustrated in FIG. 2, using one or a pair of strain gauges disposed on any one or both of a front and a rear of the flexible device in each disposition position. As described above, the measurement unit of FIG. 2 may amplify the voltage output using the amplifier 220, and may convert the amplified voltage into a digital value using the ADC 230.

In most cases, sensors like the strain gauges may generate analog outputs, so the sensors may convert the analog outputs into a digital value using hardware such as an ADC, and then use the digital value. The sensor value converted in this process may have noise components unrelated to the actual signal components, so the noise components may be separated from the signal components by a noise filter, according to an embodiment of the present disclosure as described above, prior to the utilization of the measured sensor value. For example, a change in a shape of a mobile device, the change being caused by the user, may involve components of a low frequency of less than 5 Hz. Therefore, noise signals comprised of components of a frequency higher than 5 Hz may be effectively removed using a low-pass filter, so the noise filter may be implemented using the low-pass filter.

Figure 7:
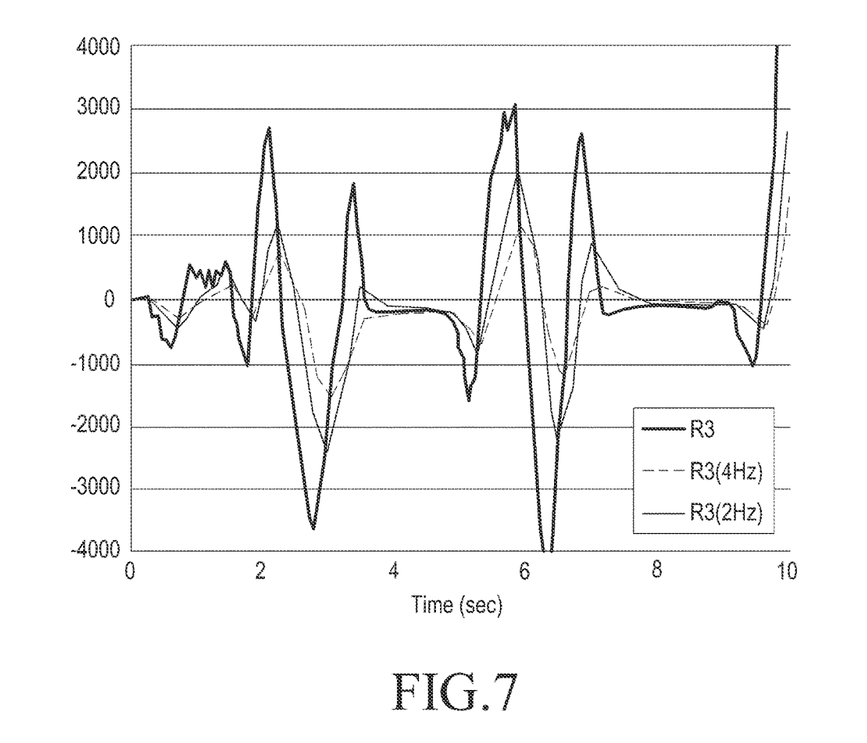
FIG. 7 is a graph illustrating results obtained by applying a noise filter according to an embodiment of the present disclosure.

FIG. 7 is a graph illustrating results obtained by applying a noise filter according to an embodiment of the present disclosure.

Referring to FIG. 7, a comparison between an output voltage level of one channel, which was measured for 10 seconds, and output voltage levels of a low-pass filter having a cut-off frequency of 2 Hz and 4 Hz, respectively, are illustrated.

With respect to FIG. 7, it may be noted that an output signal of the noise filter is smoother as the noise filter has a lower cut-off frequency, e.g., 2 Hz rather than 4 Hz. In FIG. 7, a horizontal axis represents time, and a vertical axis represents a value determined by subtracting a value, e.g., 8192±10%, which is given when there is no bending, from a 14-bit value, e.g., 0 to 16383, which is obtained by an ADC.

Although it is shown in FIG. 4 that the output of the noise filter 402 is connected to an input of the channel compensator 403, an order of the function blocks may be subject to change according to an embodiment of the present disclosure. For example, the channel compensator 403 may be situated in front of the noise filter 402.

The channel compensator 403, as described above, may be used to compensate for different sensitivities of the sensors, such as the strain gauges. In some cases, analog sensors may perform slightly different operations due to the fine tolerances, even though the analog sensors are manufactured by a same process and mounted on each flexible device. In order to solve this problem, if a significant error occurs in a sensor output due to a deviation between channels, e.g., a disposition regions for sensors, the channel compensator 403 may obtain and store channel deviation information in advance by online and/or offline calibration, and then compensate the sensor output using the stored channel deviation information. For example, if an output of any strain gauge channel that is bent with the same radius of curvature appears to be 50% less than that of a reference channel, the channel compensator 403 may compensate for the deviation between the strain gauge channel and the reference channel by outputting the results obtained by multiplying the sensor value measured in the same channel by 2 in a subsequent compensation operation.

The curve point detector 404 may detect information about a curved section appearing in each of edge regions, e.g., first to fourth outer regions, according to the output values of the sensors, which are disposed in a row on each edge of the flexible device 100. A definition of the curved section and/or the type of the detected information may be slightly different according to various implementations.

For example, if a region having a same bending direction in a specific edge is defined as one curved section, sensors that consecutively have a same sign for output values may form one curved section. Very fine bending is may be a meaningless or insignificant change, and the user may have difficulty in inputting an insignificant change. Therefore, in accordance with an embodiment of the present disclosure, if a sum of sensor output values in the curved section is less than or equal to a threshold, the curved section may be ignored. Since one or more curved sections may occur in one outer region, the curve point detector 404 should detect and process curve points, taking this into consideration.

After finding the curved section, the curve point detector 404 may find a position of the point that may represent each curved section. In the present disclosure, this is called a 'curve point'. The curve point may be defined as a point, e.g., a point having a largest sensor value in the curved section, having a smallest radius of curvature according to an embodiment of the present disclosure, and/or may also be defined as a center of mass for a section that is bent in a same direction.

Figure 8A:
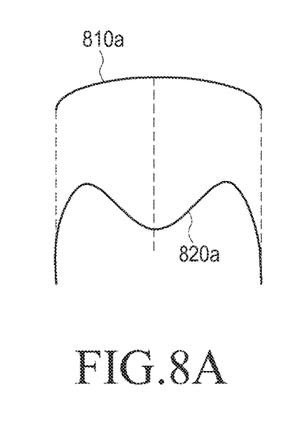
FIGS. 8A, 8B, and 8C illustrate different examples of a relationship between a curved section's shape and a sensor output in a flexible device according to an embodiment of the present disclosure.
Figure 8B:
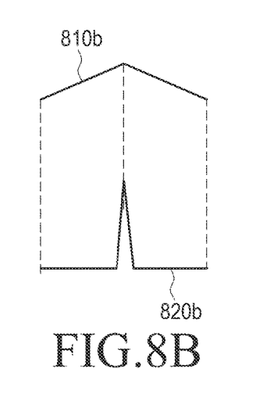
Figure 8C:
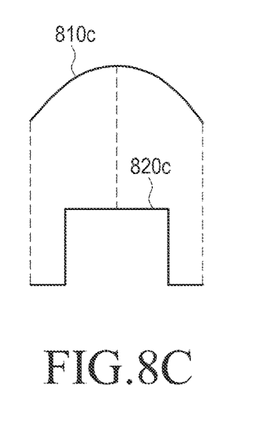

FIGS. 8A, 8B, and 8C illustrate different examples of a relationship between a curved section's shape and a sensor output in a flexible device according to an embodiment of the present disclosure.

Referring to FIGS. 8A to 8C, shapes 810a, 810b and 810c of three different curved sections occurring due to bending of a flexible device are illustrated, and output values 820a, 820b and 820c of sensors disposed on an edge in a row, for their associated shapes, are illustrated according to an embodiment of the present disclosure.

Referring to FIGS. 8A to 8C, it may be noted that a representative point, e.g., a curve point, of the curved section may not correspond to the point, e.g., a point having the smallest radius of curvature, having the largest sensor value in the curved section. For example, two points in one curved section may have the largest sensor value, e.g., the smallest radius of curvature, in the case of FIG. 8A, and there are many points having the largest sensor value, e.g., the smallest radius of curvature, in the case of FIG. 8C. Therefore, as an example of a method for effectively selecting curve points, a weighted average may be used according to an embodiment of the present disclosure.

The weighted average may be calculated using Equation (3) below.

$$x = \frac{\sum_{i \in S} \omega_i x_i}{\sum_{i \in S} \omega_i} \qquad \text{Equation (3)}$$

where x denotes a weighted average calculated for outer regions 110, 111, 112 and 113 of each side and/or edge, and if positions of first to N-th sensors on each side are determined, S represents an index set of $\{1, \ldots, N\}$. By calculating a weighted average for each of the outer regions 110, 111, 112 and 113 using Equation (3), the curve points may be accurately determined based only on the sensor values as in FIGS. 8A and 8C.

In Equation (3), $x_i$ denotes a position of a sensor, and a variety of coordinate systems may be used. For example, a distance to the reference point may be expressed in millimeters (mm), and if sensors are disposed at regular intervals, coordinates may be used as sensor numbers. In addition, $\omega_i$ denotes an angle at which a sensor is bent, the angle being calculated based on the output of an i-th sensor.

Therefore, in accordance with an embodiment of the present disclosure, a curve point may be defined as a center of mass for a section that is bent in a same direction, making it possible to find a more accurate position, e.g., a position that is determined to better reflect the user's intentions, compared to when the curve point is defined as a point at which a flexible device is most severely bent.

If the curve point detector 404 has completed the detection of curve points appearing on each side and/or outer region, then the bending line detector 406 may detect a bending line according to the detection results. A method of detecting a bending line according to the detected curve points may be implemented in various ways. For example, in accordance with an embodiment of the present disclosure, the curve points may be connected by a line based on their different priorities depending on the number of curve points appearing on each side and/or outer region.

More specifically, in a case where one curve point is detected in each of the first and second outer regions 110 and 111, as shown in FIG. 1, if the two curve points have a same direction, then they may be determined to be one bending line. On the other hand, if the two curve points are different in direction, they may not be determined as a bending line. As another example, in a case where two curve points, having different directions, appear in the first outer region 110 or the second outer region 111, and one curve point appears in another outer region, e.g., the third outer region 112 or the fourth outer region 113, a line connecting two curve points having the same direction may be determined to be a bending line. In this way, a determination method appropriate for the case where a different number of curve points appear on each side and/or edge may be derived and applied. The aforesaid method may be effectively applied only for the case where sensors are disposed along edges of the flexible device according to an embodiment of the present disclosure.

Figure 9:
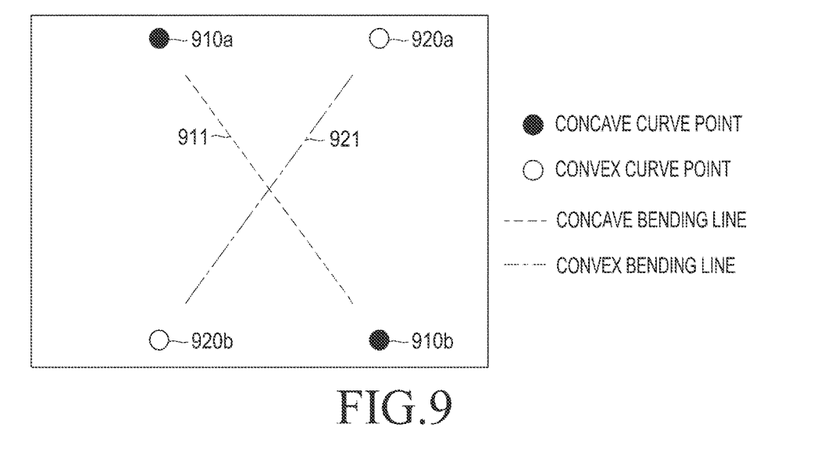
FIG. 9 illustrates an example of detecting bending lines according to an embodiment of the present disclosure.
Figure 10:
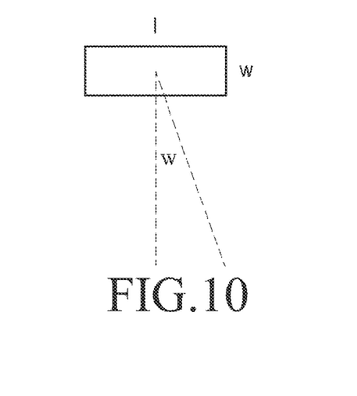
FIG. 10 illustrates a strain gauge and a slope of a bending line according to an embodiment of the present disclosure.

FIG. 9 illustrates an example of detecting bending lines according to an embodiment of the present disclosure; and FIG. 10 illustrates a strain gauge and a slope of a bending line according to an embodiment of the present disclosure.

Referring to FIGS. 9 and 10, if two curve points occur in each of an upper outer region and a lower outer region, one of concave curve points 910a and 910b, and one of convex curve points 920a and 920b, may appear in each outer region. Accordingly, if associated curve points in the upper outer region and the lower outer region are connected, a concave bending line 911 and a convex bending line 921 may be detected. This situation may occur when the flexible device is twisted.

However, if a bending line is detected only with the sensors disposed on edges of the flexible device, according to an embodiment of the present disclosure, it may not be possible to accurately determine, based only on the values measured by the sensors, whether a concave bending line formed by connecting concave curve points has occurred, or a convex bending line formed by connecting convex curve points has occurred. In this case, priority of connecting curve points may be determined in advance, and a line connecting the curve points may be determined as a high-priority line.

If a bending line is detected by the bending line detector 406, then the feature extractor 408 may calculate a variety of information, such as a position, a slope, an angle, a thickness and a direction of the bending line. If the bending line detector 406 detects a bending line according to the results obtained by compensating for a deviation between sensors, the feature extractor 408 may calculate information such as a position, a slope, an angle, a thickness and a direction of the bending line.

However, since a total angle at which the flexible device is bent along the lending line may be affected by the output values of sensors and also by a slope of the bending line as described above, a slope compensation process is needed for accurate calculation of an angle at which the flexible device is bent along the lending line. Therefore, the slope compensator 407 may perform the slope compensation process according to an embodiment of the present disclosure. In this case, as shown in FIG. 4, the slope compensator 407 may be exchanged with the feature extractor 408 with respect to the processing order.

Prior to a description of a method of compensating for an influence of an angle due to a slope of a bending line in the slope compensator 407, the influence that the slope of the bending line exerts on the output of the sensor may be as follows.

The strain gauge is a sensor that represents a physical strain, which is caused in the sensor by a force such as a bending force and a straining force, as a change in resistance between both ends of the sensor, and active direction of the force may be determined.

Therefore, in a case of a strain gauge having a pattern in which a direction in an active direction is represented by 1 and a width is represented by w, as illustrated in FIG. 10, if the slope of the bending line is given as φ, strain $\varepsilon_l$ in the active direction and strain $\varepsilon_w$ in the vertical direction may be expressed as Equation (4) and Equation (5), respectively, and a change ΔR in resistance between both ends of the sensor based on these two components may be expressed as Equation (6) below, in which v denotes a Poisson's ratio of a material.

$\varepsilon_l = \varepsilon |\cos \phi|$  Equation (4)

$\varepsilon_w = \varepsilon |\sin \phi|$  Equation (5)

$\Delta R \approx R((1+2v)\varepsilon_l - \varepsilon_w) = R\varepsilon((1+2v)|\cos \phi| - |\sin \phi|)$  Equation (6)

A slope compensation method that takes into account these characteristics of the strain gauge may be as follows. A plurality of sensors may be disposed on a wide plate having a same material and thickness as a flexible device, and then bent with a predetermined radius of curvature. In this case, a sensor's output α, obtained by bending the sensor in the active direction, and a sensor's output β, obtained by bending the sensor in the vertical direction, may be stored, and then, a sensor output ΔV', compensated by Equation (7) below, may be calculated for the slope φ of the bending line.

$$\Delta V' = \frac{\Delta V}{|\cos\phi| - \frac{\beta}{\alpha}|\sin\phi|}$$  Equation (7)

If the slope compensation is completed by the slope compensator 407 as described above, the feature extractor 408 may extract at least one value that may be a feature of the bending line.

As an example, assuming that a plurality of sensors are disposed on the flexible device at regular intervals, as shown in FIG. 1, coordinates may be set for each of the sensors.

Figure 11:
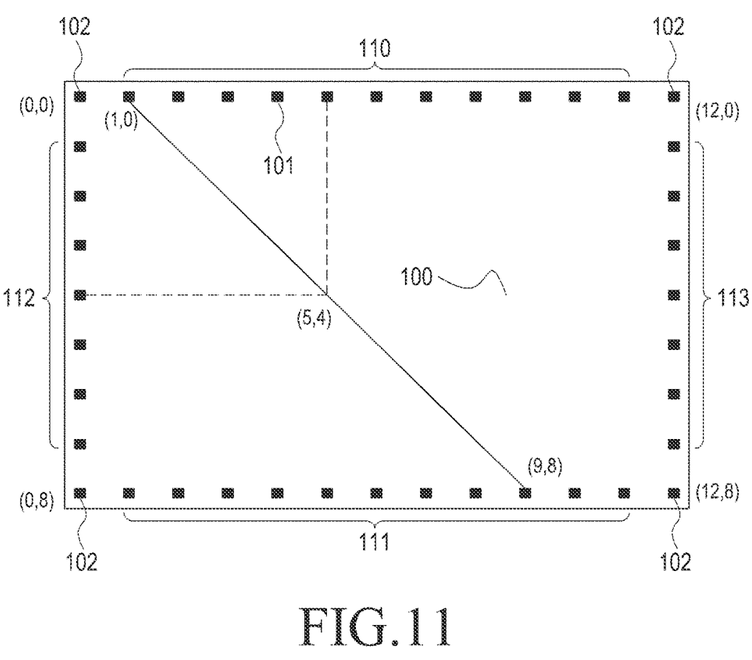
FIG. 11 illustrates an example of extracting features by detecting a bending line in a flexible device according to an embodiment of the present disclosure.

FIG. 11 illustrates an example of extracting features by detecting a bending line in a flexible device according to an embodiment of the present disclosure.

Referring to FIG. 11, coordinates of a corner sensor 102, which is situated in the upper left corner, may be represented as (0,0), coordinates of a corner sensor 102, which is situated in the upper right corner, may be represented as (12,0), coordinates of a corner sensor 102, which is situated in the lower left corner, may be represented as (0,8), and coordinates of a corner sensor 102, which is situated in the lower right corner, may be represented as (12,8).

For example, assuming that a curve point, at which the flexible device is bent inward by 40°, is detected in a position, e.g., the width of its curved section is assumed to be 2, of (1,0) on the upper left, and a curve point, at which the flexible device is bent inward by 60°, is detected in a position, e.g., the width of its curved section is assumed to be 4 of (9,8) on the lower right, a position of the bending line may be calculated as (5,4) which is a middle point between (1,0) and (9,8), and a slope of the bending line may be 45° because the bending line is tilted clockwise, which may be defined as a positive number, by 45° with respect to the vertical line.

A bending angle of the bending line may be 50°, which is an average of the bending angles of 40° and 60°, for the two curve points. A thickness of the bending line may be set as 3, which is an average of 2 and 4, which are widths of the two curved sections. Finally, a direction of the bending line may be inward.

As is apparent from the foregoing description, an aspect of the present disclosure may provide a plurality of bending sensors disposed on edges of a flexible device and which may detect a bending line by detecting curve points on the flexible device using the plurality of sensors in order to accurately detect a strained shape of a flexible device.

An aspect of the present disclosure may detect bending of a flexible device and may also detect a more accurate and precise position and degree of the bending, even though flexible devices are different in device thickness and bending strength.

An aspect of the present disclosure may provide a plurality of bending sensors disposed on edges of a flexible device and may detect curve points on the flexible device based on values measured by the plurality of disposed sensors in order to obtain more accurate information about a bending line.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A flexible device comprising:
a measurement unit including a plurality of bending sensors disposed along at least one edge of the flexible device, and configured to output measurement values sensed by the plurality of bending sensors; and
a controller configured to:
detect a position of at least one curve point on the flexible device by receiving the sensed measurements values from the measurement unit,
detect at least one bending line of the flexing device according to information about positions of curve points which are detected on at least two different sides of the flexible device, and
determine at least one feature of the at least one bending line based at least in part on at least one feature for the at least one curved point,
wherein the controller includes a channel compensator configured to compensate for a deviation between the plurality of bending sensors disposed on the flexible device.

2. The flexible device of claim 1,
wherein the measurement unit further includes at least one sensor disposed in a corner of the flexible device, and
wherein the controller is configured to detect bending of the corner by receiving a measurement value sensed by the sensor disposed in the corner.

3. The flexible device of claim 1, wherein the sensor is disposed in a specific direction in order to detect a change of a shape of the flexible device that is bent perpendicularly to one side on an edge of the flexible device.

4. The flexible device of claim 1, wherein the plurality of bending sensors includes two bending sensors that are disposed in a pair on at least one of a front and a rear of the flexible device in each disposition position.

5. The flexible device of claim 1, wherein the measurement unit includes a bridge circuit configured to output a voltage value according to a change in resistance of the bending sensor.

6. The flexible device of claim 5, wherein the measurement unit includes:
an amplifier configured to amplify an output voltage value of the bridge circuit; and
an analog-to-digital converter configured to convert an analog signal amplified by the amplifier into a digital signal.

7. The flexible device of claim 1, wherein the controller further includes:
a curve point detector configured to detect a position of the at least one curve point on the flexible device by receiving a sensed measurement value from the measurement unit;
a bending line detector configured to detect the at least one bending line of the flexible device according to the position information of curve points which are detected on the at least two different sides of the flexible device by the curve point detector; and
a feature extractor configured to extract information about at least one feature for the at least one bending line detected by the bending line detector.

8. The flexible device of claim 7, wherein the information extracted by the feature extractor includes at least one of a position, a slope, an angle, a thickness and a direction of the at least one bending line.

9. The flexible device of claim 7, wherein the controller further includes a noise filter configured to filter the sensed measurement value using a low-pass filter.

10. The flexible device of claim 7, wherein the controller further includes a gain controller configured to adjust an output value of the measurement unit, by controlling a gain of an amplifier included in the measurement unit, if it is determined, according to an output value of the curve point detector, that an output value of each of the plurality of bending sensors does not satisfy a preset threshold.

11. The flexible device of claim 7, wherein the controller further includes a slope compensator configured to compensate bending information of the at least one bending line using slope information of the at least one bending line detected by the bending line detector.

* * * * *